US012571151B2

(12) United States Patent
Choe

(10) Patent No.: US 12,571,151 B2
(45) Date of Patent: Mar. 10, 2026

(54) LAUNDRY DRYER AND LAUNDRY DRYER CONTROL METHOD

(71) Applicant: LG Electronics Inc., Seoul (KR)

(72) Inventor: Woonje Choe, Seoul (KR)

(73) Assignee: LG Electronics Inc., Seoul (KR)

( * ) Notice: Subject to any disclaimer, the term of this patent is extended or adjusted under 35 U.S.C. 154(b) by 490 days.

(21) Appl. No.: 17/909,261

(22) PCT Filed: Feb. 26, 2021

(86) PCT No.: PCT/KR2021/002436
§ 371 (c)(1),
(2) Date: Sep. 2, 2022

(87) PCT Pub. No.: WO2021/177671
PCT Pub. Date: Sep. 10, 2021

(65) Prior Publication Data
US 2023/0087630 A1     Mar. 23, 2023

(30) Foreign Application Priority Data

Mar. 4, 2020    (KR) ........................ 10-2020-0027379

(51) Int. Cl.
*D06F 35/00*          (2006.01)
*A61L 2/07*           (2006.01)
(Continued)

(52) U.S. Cl.
CPC .............. *D06F 35/008* (2013.01); *A61L 2/07* (2013.01); *D06F 58/02* (2013.01); *D06F 58/206* (2013.01);
(Continued)

(58) Field of Classification Search
None
See application file for complete search history.

(56) References Cited

U.S. PATENT DOCUMENTS

2006/0117596 A1* 6/2006 Kim ........................ D06F 33/65
                                                           34/607
2009/0255141 A1* 10/2009 Moon ..................... D06F 58/10
                                                           34/202
(Continued)

FOREIGN PATENT DOCUMENTS

CN     113279226 A     8/2021
EP     1746194 A2     1/2007
(Continued)

OTHER PUBLICATIONS

Extended European Search Report in European Appln. No. 21764747.8, mailed on Mar. 5, 2024, 15 pages.
(Continued)

*Primary Examiner* — Omair Chaudhri
(74) *Attorney, Agent, or Firm* — Fish & Richardson P.C.

(57) ABSTRACT

A laundry dryer control method includes a sterilizing drying step of increasing the internal temperature of a cabinet for sterilization, a steam-washing step of supplying steam into a drum to sterilize the drum after the sterilizing drying step, and a blowing step of circulating air inside the drum after the steam-washing step. The temperature of the drum is controlled to be greater than or equal to a reference temperature for sterilization.

7 Claims, 9 Drawing Sheets

(51) Int. Cl.

| | |
|---|---|
| *D06F 58/02* | (2006.01) |
| *D06F 58/20* | (2006.01) |
| *D06F 58/24* | (2006.01) |
| *D06F 58/45* | (2020.01) |
| *D06F 101/20* | (2020.01) |

(52) U.S. Cl.
CPC .............. *D06F 58/24* (2013.01); *D06F 58/45* (2020.02); *D06F 2101/20* (2020.02)

(56) References Cited

U.S. PATENT DOCUMENTS

| | | | | |
|---|---|---|---|---|
| 2009/0320322 A1* | 12/2009 | Kim | ........................ | D06F 58/44 700/275 |
| 2011/0005279 A1* | 1/2011 | Yoo | ........................ | D06F 34/22 68/5 C |
| 2011/0277334 A1* | 11/2011 | Lee | ........................ | D06F 58/206 34/73 |
| 2017/0233918 A1* | 8/2017 | Lee | ........................ | D06F 58/24 68/5 C |
| 2020/0354881 A1* | 11/2020 | Zheng | ........................ | D06F 58/38 |

FOREIGN PATENT DOCUMENTS

| | | | | |
|---|---|---|---|---|
| EP | 2325375 B1 * | 11/2016 | ........... | D06F 35/008 |
| EP | 3868948 | 8/2021 | | |
| JP | 2005253584 | 9/2005 | | |
| JP | 2019-158173 A | 9/2019 | | |
| JP | 2020-014703 A | 1/2020 | | |
| JP | 2020028542 | 2/2020 | | |
| KR | 10-0531335 B1 | 11/2005 | | |
| KR | 20060085960 A * | 7/2006 | ............ | D06F 33/69 |
| KR | 10-2006-0101951 | 9/2006 | | |
| KR | 100624719 | 9/2006 | | |
| KR | 20070089535 A * | 8/2007 | ............ | D06F 33/43 |
| KR | 20090105298 | 10/2009 | | |
| KR | 10-2010-0001439 A | 1/2010 | | |
| KR | 10-2017-0006556 A | 1/2017 | | |
| KR | 20180013535 | 2/2018 | | |
| WO | WO 2017/036560 | 3/2017 | | |

OTHER PUBLICATIONS

International Search Report and Written Opinion in International Appln. No. PCT/KR2021/002436, dated Jun. 18, 2021, 18 pages (with English translation).

Notice of Allowance in Korean Appln. No. 10-2020-0027379, mailed on May 7, 2025, 5 pages (with English translation).

Office Action in Chinese Appln. No. 202180018783.4, mailed on May 27, 2025, 13 pages (with English translation).

* cited by examiner

Figure 5A:
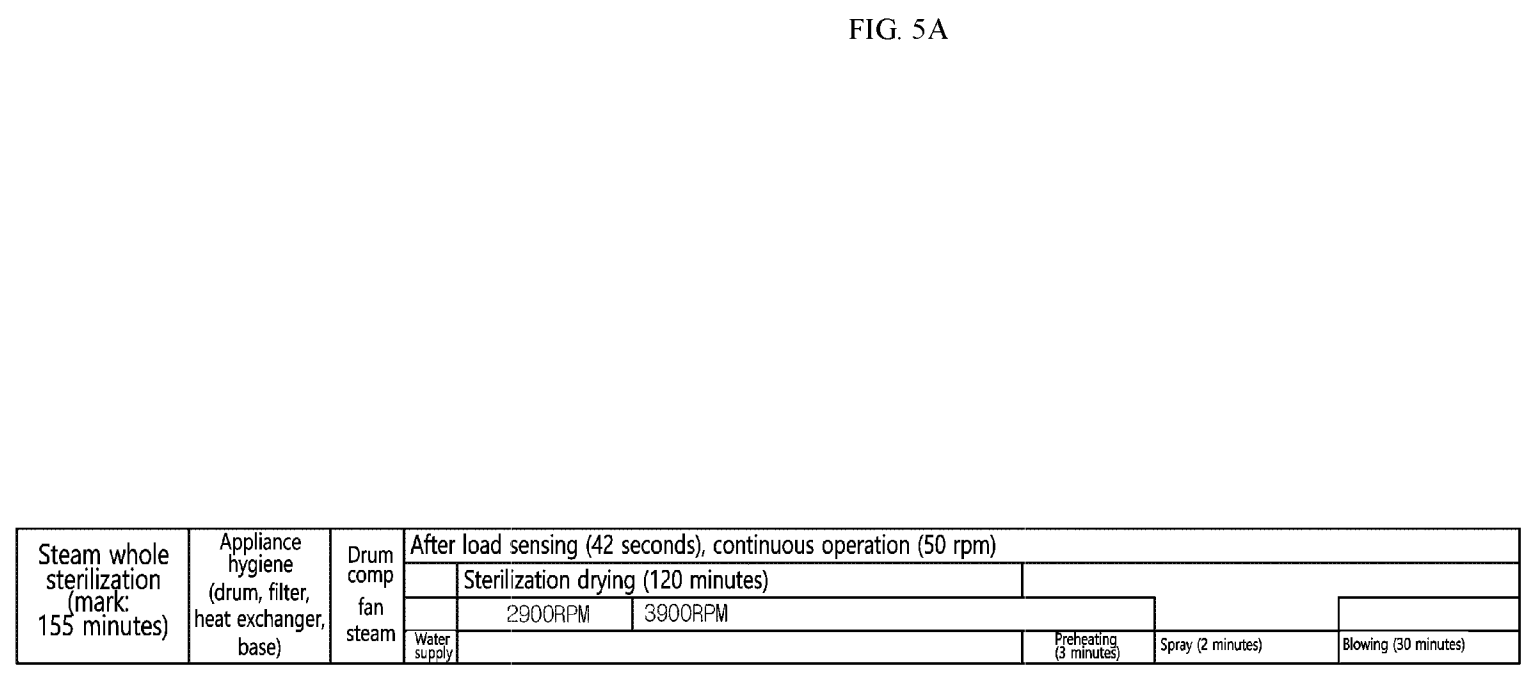

| Steam whole sterilization (mark: 155 minutes) | Appliance hygiene (drum, filter, heat exchanger, base) | Drum comp | After load sensing (42 seconds), continuous operation (50 rpm) | | |
|---|---|---|---|---|---|
| | | | Sterilization drying (120 minutes) | | |
| | | fan | 2900RPM | 3900RPM | |
| | | steam | Water supply | | |
| | | | | Preheating (3 minutes) | Spray (2 minutes) | Blowing (30 minutes) |

LAUNDRY DRYER AND LAUNDRY DRYER CONTROL METHOD

CROSS-REFERENCE TO RELATED APPLICATIONS

This application is a National Stage application under 35 U.S.C. § 371 of International Application No. PCT/KR2021/002436, filed on Feb. 26, 2021, which claims the benefit of Korean Application No. 10-2020-0027379, filed on Mar. 4, 2020. The disclosures of the prior applications are incorporated by reference in their entirety.

TECHNICAL FIELD

The present disclosure relates to a laundry dryer and a method for controlling the laundry dryer, and more particularly, to a laundry dryer and a method for controlling the laundry dryer for generating high-temperature steam via a steam generator and controlling rotation of a drum and rotation of a fan independently.

BACKGROUND

A laundry treating apparatus may perform a drying cycle for removing moisture from laundry. For example, a laundry treating apparatus may shorten a drying time of the laundry and perform sterilization and disinfection of the laundry by supplying hot air to a drum for accommodating therein the laundry to dry the laundry.

In some cases, the laundry treating apparatus for performing the drying cycle also includes a laundry treating apparatus for supplying steam to the laundry in order to remove wrinkles of the laundry, improve a drying efficiency, or perform the sterilization or the like.

In some cases, a condensing dryer may be equipped with a heat pump system.

In some cases, the condensing dryer may have contamination issues caused by condensate. Specifically, foreign substances including lint generated from an object-to-be-dried may adhere to the drum, or the contamination may occur from bacteria present in a heat exchange assembly or the like due to prolonged use of the dryer.

In some cases, the drum may be washed directly in order to solve such problem, but the washing of the drum disposed inside may be inconvenient for a user because of a structure of the dryer.

SUMMARY

The present disclosure describes a configuration and a method that can automatically wash a drum.

According to one aspect of the subject matter described in this application, a laundry dryer includes a cabinet that defines an outer appearance of the laundry dryer, a drum rotatably disposed inside the cabinet, a duct assembly configured to guide air discharged from the drum and to supply the air to the drum, a circulation fan configured to cause the air to move along the duct assembly, a heat exchange assembly disposed in the duct assembly and configured to exchange heat with the air in the duct assembly, a compressor configured to compress refrigerant to enable heat exchange between the refrigerant and the air in the duct assembly, a steam supply configured to supply steam into the drum, and a controller configured to control the drum, the circulation fan, the compressor, and the steam supply. The controller is configured to drive the compressor to increase a temperature inside the cabinet and then operate the steam supply to sterilize an inside of the drum by increasing an amount of heat supplied to the inside the drum.

Implementations according to this aspect can include one or more of the following features. For example, the controller can be configured to perform a sterilization operation of the drum based on no load being applied to the drum. In some examples, the controller can be configured to operate the drum and the circulation fan while the compressor operates. In some examples, the controller can be configured to operate the steam supply after stopping operation of the compressor.

In some implementations, the controller can be configured to, while the steam supply operates, rotate the drum and stop operation of the circulation fan. In some examples, the steam supply can be configured to receive and store a preset amount of water, and based on receiving power, heat the water to thereby generate steam for a preset steam spray time. In some cases, the steam supply can be configured to heat the water while operation of the circulation fan is stopped. In some implementations, the controller can be configured to operate the circulation fan after stopping operation of the steam supply.

In some implementations, the laundry dryer can include a drain pump configured to cause condensate water collected in the cabinet to move out of the cabinet, wherein the controller can be configured to control the drain pump. The controller can be configured to stop operation of the steam supply and then operate the drain pump for a preset drainage time.

According to another aspect, a method for controlling a laundry dryer, which includes a cabinet and a drum disposed inside the cabinet, includes increasing a temperature inside the cabinet for sterilization of the drum, supplying steam into the drum for sterilization of the drum after increasing the temperature inside the cabinet, and circulating air inside the drum after supplying the steam into the drum.

Implementations according to this aspect can include one or more of the following features. For example, increasing the temperature inside the cabinet includes driving a compressor to thereby increase the temperature inside the cabinet. In some examples, increasing the temperature inside the cabinet can include operating a circulation fan to thereby circulate heated air through the drum. In some examples, increasing the temperature inside the cabinet can include rotating the drum to thereby heat an inside of the drum.

In some implementations, supplying the steam into the drum can include operating a steam supply to supply the steam into the drum. In some examples, supplying the steam into the drum can include preheating the steam supply and spraying the steam into the drum. In some examples, supplying the steam into the drum can include rotating the drum to thereby sterilize an inside of the drum.

In some implementations, increasing the temperature inside the cabinet can include operating a circulation fan to thereby circulate heated air through the drum, where supplying the steam into the drum can include rotating the drum to thereby sterilize an inside of the drum, and stopping operation of the circulation fan.

In some examples, circulating the air inside the drum can include rotating a circulation fan to thereby circulate heated air through the drum. In some implementations, circulating the air inside the drum can include operating a drain pump to thereby drain condensate water collected in the cabinet.

In some examples, increasing the temperature inside the cabinet can include increasing the temperature of the cabinet until a temperature of a heat exchange assembly becomes greater than or equal to 60 degrees Celsius, where the heat exchange assembly is disposed at a position receiving air discharged from the drum.

In some implementations, the temperature of the drum can be controlled to become the temperature equal to or higher than the reference temperature at which the sterilization is performed, thereby sterilizing the drum.

In some implementations, the surface temperature of the drum can be raised to the temperature equal to or higher than the reference temperature at which the sterilization is performed via the driving control of the compressor, so that the drum can be simply sterilized without a separate component/device for the sterilization.

BRIEF DESCRIPTION OF DRAWINGS

FIG. 3 is a block diagram illustrating an example of a control configuration of the laundry dryer.

FIGS. 5A and 5B respectively show examples of a steam drying method.

DETAILED DESCRIPTION

Figure 1:
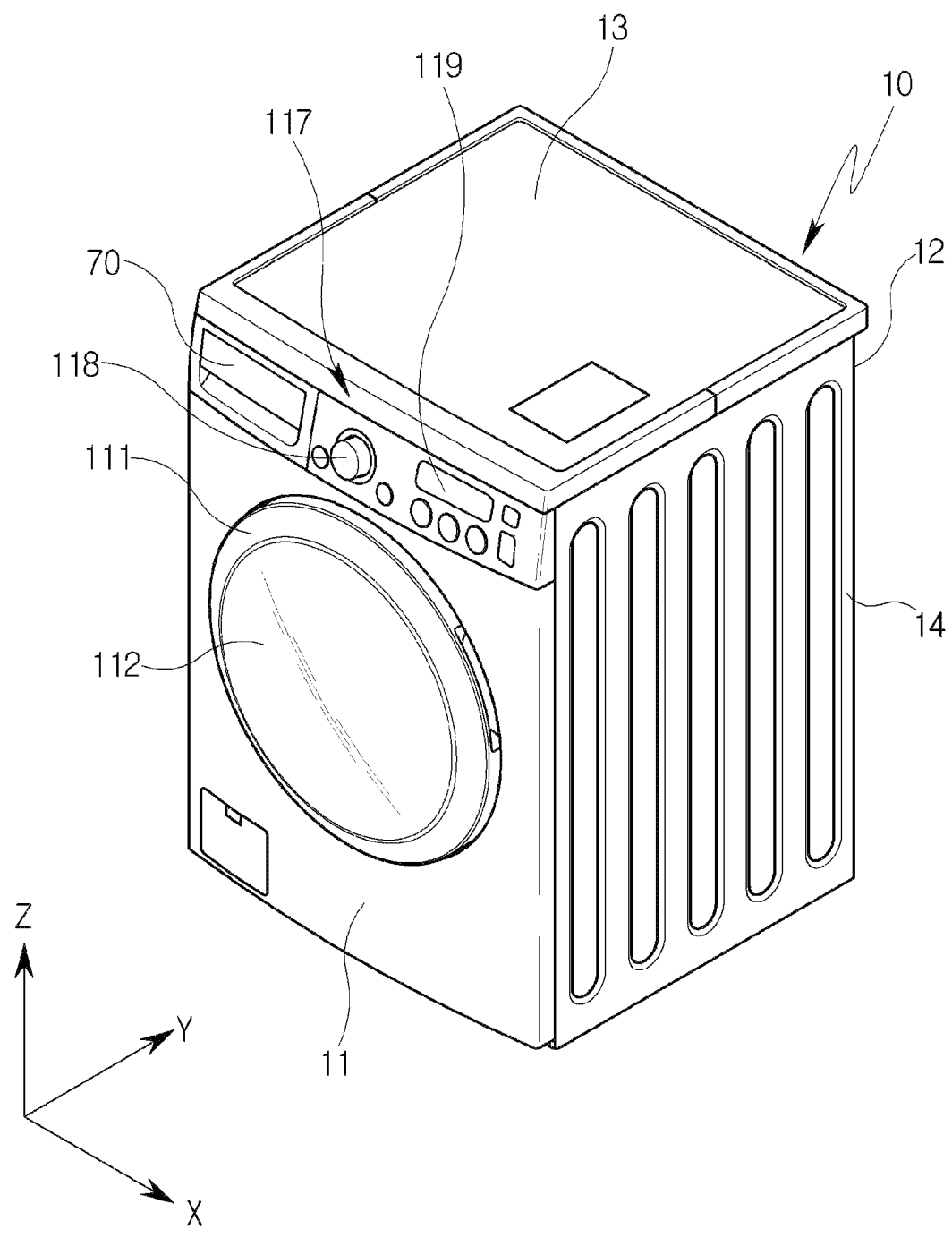
FIG. 1 is a view for illustrating an outer appearance of an example of a laundry dryer.

Hereinafter, one or more implementations of the present disclosure will be described in detail with reference to the accompanying drawings. FIG. 1 is a view illustrating an outer appearance of an example of a laundry dryer, and FIG. 2 is a cross-sectional view illustrating an example of an internal structure of the laundry dryer.

Figure 2:
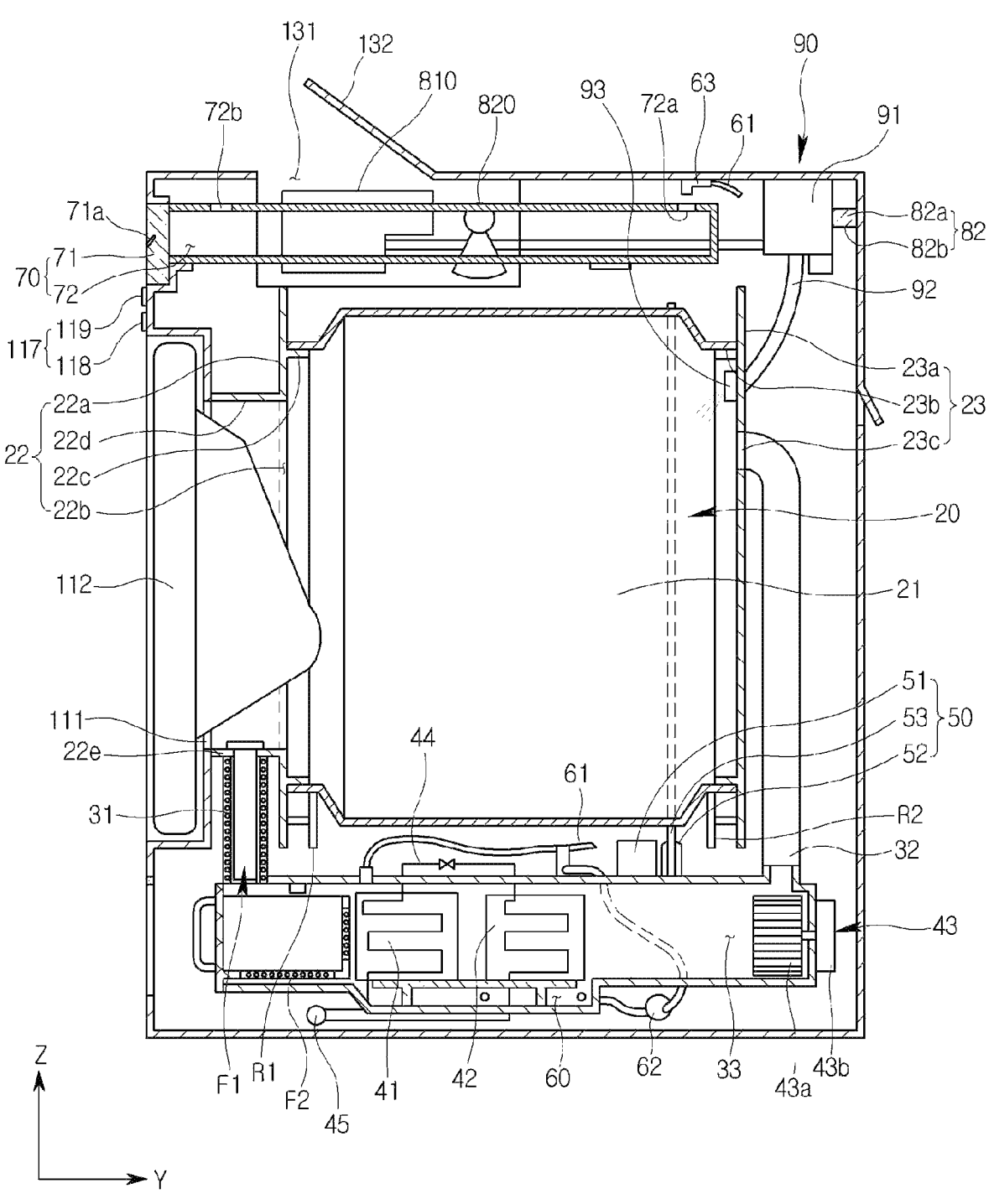
FIG. 2 is a cross-sectional view for illustrating an example of an internal structure of the laundry dryer.

As shown in FIGS. 1 and 2, in some implementations, a cabinet 10 defines an outer body of a laundry dryer 1 and includes a front panel 11 defining a front surface of the laundry dryer 1, a rear panel 12 defining a rear surface of the laundry dryer 1, a pair of side panels 14 defining side surfaces of the laundry dryer 1, and a top panel 13 defining a top surface of the laundry dryer 1.

The front panel 11 can include an inlet 111 defined therein to be in communication with a drum 20 to be described later, and a door 112 pivotally coupled to the cabinet 10 to open and close the inlet 111.

In some examples, a control panel 117 can be disposed on the front panel 11.

For example, the control panel 117 can include input device 118 for receiving a control command from a user, output device 119 for outputting information such as the control command or the like selectable by the user, and a main controller that controls a command to perform a cycle of the laundry dryer 1.

In some examples, the input device 118 can include a power supply requesting device for requesting power supply to the laundry dryer, a course input device for allowing the user to select a course among multiple courses, an execution requesting device for requesting start of the course selected by the user, and the like.

The output device 119 can include at least one of a display panel capable of outputting characters and/or figures, and a speaker capable of outputting audio signals and sounds. The user can easily identify a current situation of the ongoing cycle, a remaining time, and the like via the information output via the output device 119.

Inside the cabinet 10, there are the drum 20 rotatably disposed and providing therein a space in which laundry (an object-to-be-dried) is accommodated, a duct assembly 30 for forming a flow path for re-supplying air discharged from the drum 20 to the drum 20, and a heat exchange assembly 40 for dehumidifying and heating air introduced into the duct assembly 30 and then re-supplying the air to the drum 20.

The drum 20 includes a cylindrical drum body 21 with an open front surface. Inside the cabinet 10, a first support 22 for rotatably supporting the front surface of the drum body 21, and a second support 23 for rotatably supporting a rear surface of the drum body 21 can be disposed.

The first support 22 can include a first fixed body 22a fixed inside the cabinet 10, a drum inlet 22b defined to extend through the first fixed body 22a to allow the inlet 111 and an interior of the drum body 21 to communicate with each other, and a first support body 22c disposed on the first fixed body 22a and inserted into the front surface of the drum body 21.

The first support 22 can further include a connecting body 22d for connecting the inlet 111 and the drum inlet 22b to each other. As shown, the connecting body 22d can be formed in a pipe shape extending from the drum inlet 22b toward the inlet 111. In addition, the connecting body 22d can have an air outlet 22e in communication with the duct assembly 30.

As shown in FIG. 2, the air outlet 22e as a passage that allows internal air of the drum body 21 to flow to the duct assembly 30 can be defined as a through-hole defined to extend through the connecting body 22d.

The second support 23 includes a second fixed body 23a fixed inside the cabinet 10, and a second support body 23b disposed on the second fixed body 23a and inserted into the rear surface of the drum body 21.

The second support 23 has an air inlet 23c defined to extend through the second fixed body 23a so as to allow the interior of the drum body 21 to be in communication with the interior of the cabinet 10.

In this case, the duct assembly 30 is constructed to connect the air outlet 22e and the air inlet 23c to each other.

The cylindrical drum body 21 can be rotated via a driver 50 of various shapes.

Illustratively, in FIG. 2, an implementation in which the driver 50 includes a drum motor 51 fixed inside the cabinet 10, a pulley 52 rotated by the drum motor 51, and a belt 53 for connecting a circumferential surface of the pulley 52 and a circumferential surface of the drum body 21 to each other is shown.

In this case, the first support 22 can have a first roller R1 for rotatably supporting the circumferential surface of the drum body 21, and the second support 23 can have a second roller R2 for rotatably supporting the circumferential surface of the drum body 21.

However, the present disclosure is not limited thereto. For instance, a direct drive-type driver that rotates the drum as the drum motor 51 is directly connected to the drum without via the pulley and the belt is also applicable. This naturally falls within the scope of the present disclosure. For convenience, a description will be made based on the illustrated implementation of the driver 50.

The duct assembly 30 includes an exhaust duct 31 connected to the air outlet 22e, a supply duct 32 connected to the air inlet 23c, and a connecting duct 33 that connects the exhaust duct 31 and the supply duct 32 to each other and has the heat exchange assembly 40 installed therein.

The heat exchange assembly 40 can be formed as various apparatuses capable of sequentially dehumidifying and heating air introduced into the duct assembly 30. For example, the heat exchange assembly 40 can be formed as a heat pump system.

As the heat pump system, the heat exchange assembly 40 can include a circulation fan 43 for moving air along the duct assembly 30, a first heat exchanger (a heat absorber 41) that performs a dehumidifying function by lowering humidity of air introduced into the duct assembly 30, and a second heat exchanger (a heater 42) that is disposed inside the duct assembly 30 and heats air that has passed through the first heat exchanger 41.

The circulation fan 43 is constructed to include an impeller 43a disposed in the duct assembly 30, and an impeller motor 43b for rotating the impeller 43a, and provides a flow force to the air moving along the duct assembly 30.

The impeller 43a can be installed at any position among the exhaust duct 31, the connecting duct 33, and the supply duct 32. FIG. 2 shows an implementation in which the impeller 43a is disposed in the connecting duct 33. The present disclosure is not limited thereto, but for convenience, a description will be made below based on the implementation in which the impeller 43a is disposed in the connecting duct 33.

The heat exchange assembly 40 can exchange heat with air circulated along the duct assembly 30.

The heat absorber 41 and the heater 42 are sequentially arranged inside the connecting duct 33 along a direction from the exhaust duct 31 to the supply duct 32, and are connected to each other via a refrigerant pipe 44 for forming a circulation flow path of a refrigerant.

The heat absorber 41 is a device for cooling air and evaporating the refrigerant by transferring a heat of air introduced into the exhaust duct 31 to the refrigerant.

The heater 42 is a device for heating air and condensing the refrigerant by transferring a heat of the refrigerant that has passed through a compressor 45 to air.

The compressor 45 compresses the refrigerant that exchanges the heat with air circulated along the duct assembly 30 by receiving a rotational force by the compressor motor 45a.

In this case, moisture contained in air moves along a surface of the heat absorber 41 when passing through the heat absorber 41 and is collected on a bottom surface of the connecting duct 33.

As described above, as a configuration related to the heat exchange assembly 40 of the heat pump system type including the heat absorber 41 and the heater 42, a configuration already known in the art is applicable, and a description of a detailed configuration related thereto will be omitted.

In some examples, in order to collect condensate that is condensed from air passing through the heat absorber 41 and collected on the bottom surface of the connecting duct 33, the laundry dryer 1 has a water collecting portion 60.

The condensate condensed in the heat absorber 41 can be primarily collected in the water collecting portion 60, and then can be secondary collected in a water storage 70. The water collecting portion 60 can be located inside the connecting duct 33 as shown, or can be formed separately in a space spaced apart from the connecting duct 33.

The condensate primarily collected via the water collecting portion 60 is supplied to the water storage 70 via a condensate supply pipe 61. In some examples, the condensate supply pipe 61 has a drain pump 62 for smooth discharge of the condensate.

The water storage 70 includes a water storage tank 72 that is constructed to be extended from one side of the front panel 11 to the outside. The water storage tank 72 collects the condensate delivered from the water collecting portion 60 to be described later.

The user can extend the water storage tank 72 from the cabinet 10 to remove the condensate and then re-install the water storage tank 72 in the cabinet 10. Accordingly, the laundry dryer can be disposed at any place where a sewer or the like is not installed.

More specifically, the water storage 70 can include the water storage tank 72 that is detachably disposed in the cabinet 10 to provide a space for storing water, and an inlet 72a defined to extend through the water storage tank 72 to introduce water discharged from the condensate supply pipe 61 into the water storage tank 72.

The water storage tank 72 can be formed as a tank in a form of a drawer extendable from the cabinet 10. In this case, the front panel 11 of the cabinet has a water storage mounting hole defined therein into which the water storage tank 72 is inserted.

A panel 71 is fixed to the front surface of the water storage tank 72. The panel 71 can be detachably coupled to the water storage mounting hole to form a portion of the front panel 11.

The panel 71 can further include a groove 71a into which a user's hand is inserted to grip the panel 71. In this case, the panel 71 also functions as a handle for extending the water storage tank 72 from the cabinet or retracting the water storage tank 72 into the cabinet.

The inlet 72a is defined to receive the condensate discharged from a condensate nozzle 63 fixed to the cabinet 10. The condensate nozzle 63 can be fixed to the top panel 13 of the cabinet 10 so as to be located above the inlet 72a when the water storage tank 72 is inserted into the cabinet 10.

The user can drain water inside the water storage tank 72 by extending the water storage tank 72 from the cabinet 10 and then turning or tilting the water storage tank 72 in a direction in which the inlet 72a is located. A communication hole 72b defined to extend through a top surface of the water storage tank 72 can be further included such that water inside the water storage tank 72 is easily discharged via the inlet 72a.

In addition, the laundry dryer 1 has first filtration device F1 and second filtration device F2 as devices for removing foreign substances such as lint and dust generated in a drying process of an object to be washed such as the laundry.

The first filtration device F1 is disposed in the exhaust duct 31 to primarily filter foreign substances contained in air discharged from the drum 20.

The second filtration device F2 is disposed downstream of the first filtration device F1 in a flow direction of air so as to secondarily filter foreign substances contained in air that has passed through the first filtration device F1. In more detail, in some implementations, the second filtration device F2 can be disposed upstream of the first heat exchanger 41 inside the connecting duct 33. This is to prevent the foreign substances contained in air from accumulating in the first heat exchanger 41 acting as the heat absorber and contaminating the first heat exchanger 41 or causing performance degradation of the first heat exchanger 41.

As for detailed configurations of the first filtration device F1 and the second filtration device F2, any devices known in the art can be applied, so that a description of the detailed configurations thereof will be omitted.

In some examples, the laundry dryer 1 further includes a water supply 80 including an internal water supply 81 and an external water supply 82, and steam supply 90 for receiving water from the water supply 80 and generating steam.

The steam supply 90 can generate steam by receiving fresh water, not the condensate water. The steam supply 90 can generate steam by heating water, using an ultrasonic wave, or vaporizing water.

The steam supply 90 can be controlled to supply steam into the drum body 21 by receiving water via the external water supply 82 as well as the internal water supply 81 as needed.

The external water supply 82 can include a direct water valve 82a adjacent to the rear panel 12 or fixed to the rear panel 12, and a direct water pipe 82b for supplying water transferred from the direct water valve 82a to the steam supply 90.

The direct water valve 82a can be coupled to an external water supply source. For example, the direct water valve 82a can be coupled to a water supply pipe extending to the rear surface of the cabinet. Accordingly, the steam supply 90 can receive water directly via the direct water valve 82a.

Therefore, even when the internal water supply 81 is omitted or no water is stored in the internal water supply 81, the steam supply 90 can receive water for the steam generation via the direct water valve 82a.

The direct water valve 82a can be directly controlled by a controller 100.

The controller 100 can be installed on the control panel 117, but can be formed as a separate control panel as shown in FIG. 1 so as to prevent overload of the control panel 117 and so as not to increase a manufacturing cost.

In some examples, the controller 100 can be disposed adjacent to the steam supply 90. The controller 100 can be disposed on the side panel 14 on which the steam supply 90 is installed so as to reduce a length of a control line or the like connected to the steam supply 90.

In some examples, the steam supply 90 can be installed adjacent to the direct water valve 82a. Accordingly, residual water can be prevented from remaining in the direct water pipe 82b, and water can be supplied immediately.

The controller 100 can be configured to control an operation of the laundry dryer 1 based on an input of the user applied via the input device 118. The controller 100 can be composed of a printed circuit board and elements mounted on the printed circuit board. When the user inputs the control command such as selecting a laundry treatment course, operating the laundry dryer 1, or the like via the input device 118, the controller 100 can control the operation of the laundry dryer 1 based on a preset algorithm.

Specific control content of the controller 100 in the present disclosure will be described later. In some examples, FIG. 3 is a block diagram for illustrating a control configuration in a laundry dryer.

Figure 3:
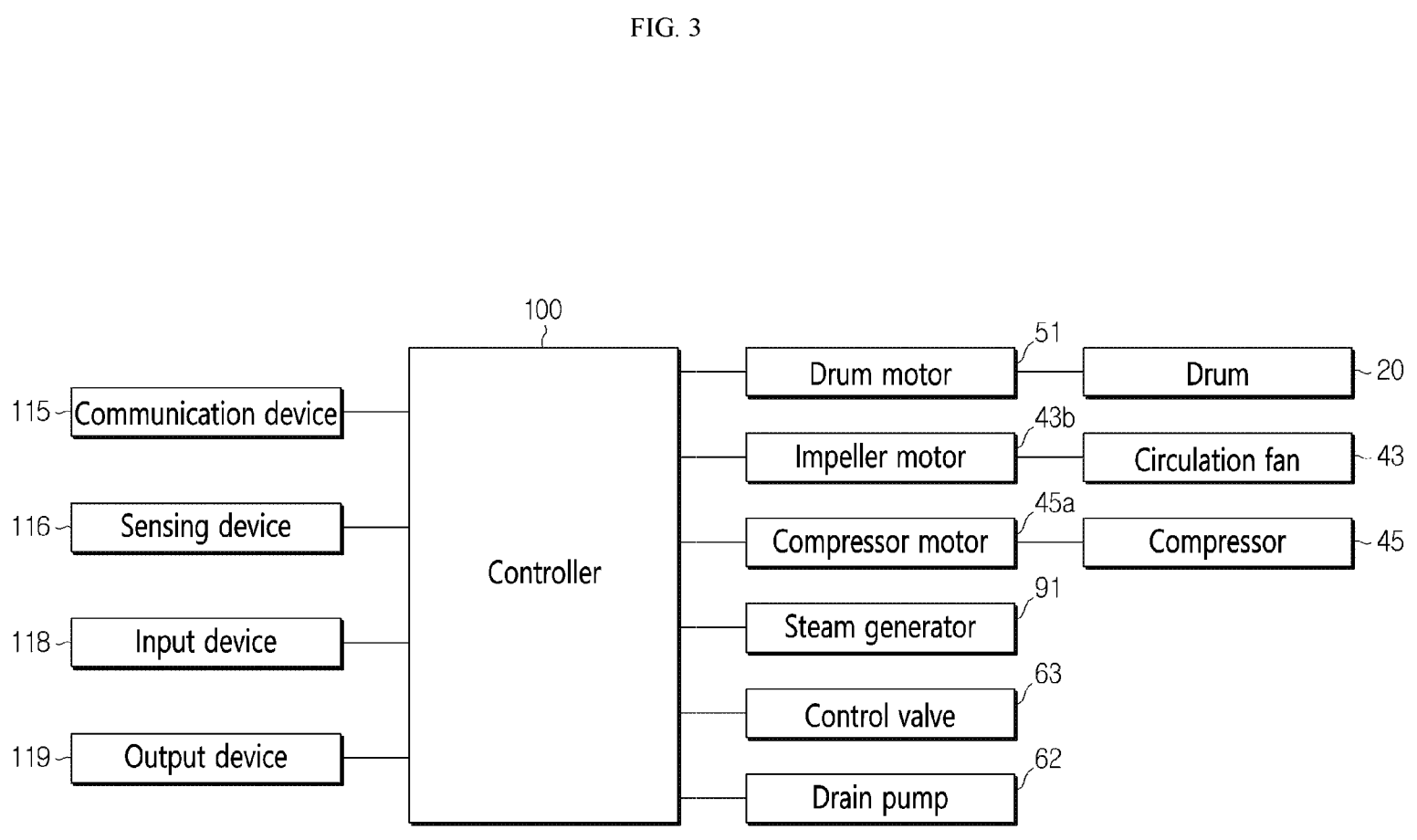

Referring to FIG. 3, the laundry dryer 1 can include at least one of the input device 118, the output device 119, communication device 115, sensing device 116, motors 51, 43b, and 45a, a drain pump 62, the steam supply 90, and the controller 100.

The input device 118 can receive a control command related to the operation of the laundry dryer 1 from the user. The input device 118 can be composed of a plurality of buttons or can be composed of a touch screen.

Specifically, the input device 118 can be formed in a shape to receive selection of a driving course of the laundry treating apparatus or receive a control input related to execution of the selected driving course.

The output device 119 can output information related to the operation of the laundry dryer 1. The output device 119 can include at least one display.

The information output by the output device 119 can include information related to an operating state of the laundry dryer 1. That is, the output device 119 can output information related to at least one of the selected driving course, whether a failure has occurred, a driving completion time, and an amount of laundry accommodated in the drum 20.

As an example, the output device 119 can be a touch screen integrally formed with the input device 118.

The communication device 115 can be in communication with an external network. The communication device 115 can receive the control command related to the operation of the laundry treating apparatus from the external network. For example, the communication device 115 can receive an operation control command of the laundry dryer transmitted from an external terminal via the external network. This allows the user to remotely control the laundry dryer.

In addition, the communication device 115 can transmit information related to an operation result of the laundry treating apparatus to a predetermined server via the external network.

In addition, the communication device 115 can be in communication with another electronic device in order to establish an Internet of Things (IoT) environment.

The sensing device 116 can sense the information related to the operation of the laundry dryer.

Specifically, the sensing device 116 can include at least one of a current sensor, a voltage sensor, a vibration sensor, a noise sensor, an ultrasonic sensor, a pressure sensor, an infrared sensor, a visual sensor (a camera sensor), an electrode sensor, and a temperature sensor.

For example, the current sensor of the sensing device 116 can sense a current flowing at a point of a control circuit of the laundry dryer 1.

As another example, the temperature sensor of the sensing device 116 can sense a temperature in the duct assembly 30 and can sense a temperature in the drum 20 according to an implementation.

As another example, the electrode sensor of the sensing device 116 can sense moisture inside the drum 20.

The sensing device 116 can include one or more temperature sensors that sense a temperature of the heat exchange assembly 40 and transmit the sensed result to the controller 100.

As an example, the sensing device 116 can include the one or more temperature sensors to sense one or more of temperatures of air and the refrigerant respectively circulating in the first heat exchanger 41 and the second heat exchanger 42.

As another example, the sensing device 116 can include the one or more temperature sensors to sense a temperature of the refrigerant circulating in the compressor 45.

The sensing device 116 can further include a plurality of temperature sensors for sensing a temperature of air flowing into or out of the drum 20.

As such, the sensing device 116 including the plurality of temperature sensors can be formed in a shape in which a sensing module for sensing the temperature is disposed in the heat exchange assembly 40 and a sensing module for receiving the sensed result of the plurality of temperature sensors and sensing the temperature is disposed in the controller 100.

As described above, the sensing device 116 can include at least one of the various types of sensors, and the types of sensors equipped in the laundry dryer 1 are not limited. In addition, the number or installation locations of respective sensors can be designed in various ways depending on a purpose.

The motors 51, 43b, and 45a can include a drum motor 51, an impeller motor 43b, and a compressor motor 45a, and can vary at least one of power, current, voltage, and speed in response to a control command (a command) of the controller 100.

For example, the drum motor 51 can vary a rotation speed (rpm) of the drum 20 in response to the control command of the controller 100.

As another example, the impeller motor 43b can vary a rotation speed (rpm) of the circulation fan 43 in response to the control command of the controller 100.

As another example, the compressor motor 45a can vary a frequency (Hz) of the compressor 45 in response to the control command of the controller 100.

In some examples, in order to drain the condensate condensed during the washing and sterilization process, the drain pump 62 serves to transfer the condensate collected in the water collecting portion 60 to the water storage 70. That is, the drain pump 62 can provide the flow force to the condensate collected in the cabinet.

The controller 100 can control a driving speed (rpm) of the drain pump 62 to drain the condensate stored after being used for the washing and the sterilization.

The steam supply 90 can be controlled to supply steam into the drum body 21 by receiving water via the external water supply 82 as well as the internal water supply 81 as needed.

The steam supply 90 can include a steam generator 91 for generating steam by heating received water, a steam pipe 92 through which the generated steam flows, and a steam nozzle 93 for spraying steam into the drum body 21.

As an example, the steam generator 91 is expressed to use a scheme (hereinafter, referred to as a 'whole heating scheme' for convenience) of generating steam by heating a certain amount of water contained therein with a heater, but is not limited thereto.

The controller 100 can control the component included in the laundry dryer 1.

First, the controller 100 can generate at least one of a power command value, a current command value, a voltage command value, and a speed command value in order to control rotation of the drum motor 51, the impeller motor 43b, and the compressor motor 45a.

In some examples, the controller 100 can control the drum motor 51, the impeller motor 43b, and the compressor motor 45a, independently.

Accordingly, the controller 100 can control an operation of at least one of the drum 20, the circulation fan 43, and the heat exchange assembly 40 based on the control input that is input to the input device 118.

That is, the controller 100 can control the rotation speed and a rotation pattern of the drum 20 based on the control input of the user input to the input device 118. In addition, the controller 100 can control the rotation speed or an operation time point of the circulation fan 43 based on the control input of the user input to the input device 118.

In addition, the controller 100 can control the heat exchange assembly 40 to adjust the temperature inside the drum 20 based on the control input of the user input to the input device 118.

For example, the controller 100 can control the driving frequency (Hz) of the compressor 45 based on the control input of the user input to the input device 118.

In addition, the controller 100 can generate at least one of the power command value, the current command value, and the voltage command value to control the operation of the steam generator 91.

That is, the controller 100 can control a heating time of the steam generator 91 based on the control input of the user input to the input device 118.

In some examples, the controller 100 can adjust the heating time of the steam generator 91 using information such as external temperature, the laundry amount, or the like.

In a case of a conventional laundry dryer, the drum and the circulation fan are connected to one motor. Therefore, the drum and the circulation fan rotated at the same time and stopped rotating at the same time.

In some examples, when spraying steam to the laundry dryer, the rotation of the circulation fan can be stopped in order to sufficiently supply the sprayed steam to the object-to-be-dried, and the drum can be also stopped to stop the circulation fan.

However, when the drum stops rotating, the object-to-be-dried is not able to be inverted. In addition, even when steam is supplied to the object-to-be-dried, steam is supplied only to objects-to-be-dried located in a direction in which steam is sprayed. Therefore, there was a limit in supplying steam evenly to entire objects-to-be-dried.

In order to solve such problem, in the laundry dryer 1, the drum motor 51 and the impeller motor 43b are formed separately from each other. In addition, the controller 100 can control the drum motor 51, the impeller motor 43b, and the compressor motor 45a, independently.

Therefore, the controller 100 can stop the rotation of the circulation fan 43 while maintaining the rotation of the drum 20 when steam is sprayed from the steam supply 90.

In addition, the controller 100 can stop the operation of the compressor 45 when operating the steam supply 90 in order to prevent the power supply from being cut off due to an instantaneous and sudden increase in power consumption of the entire laundry dryer 1.

Specifically, when operating the steam generator 91 to preheat water or generate steam, the controller 100 can stop the rotation of the compressor motor 45a.

In some examples, the controller 100 can increase the temperature inside the cabinet 10 so as to sterilize and dry the interior of the drum 20 and the duct assembly 30 and then operate the steam supply 90 to supply steam into the drum 20 so as to sterilize the interior of the drum 20 and the duct assembly 30.

While sterilizing and drying the interior of the drum 20 and the duct assembly 30, the controller 100 can operate the compressor 45 to raise the temperature inside the cabinet 10.

In some examples, the controller 100 can rotate (operate) the drum 20 and the circulation fan 43 while the compressor 45 is operating.

In some examples, after stopping the operation of the compressor 45, the controller 100 can operate the steam supply 90 so as to supply steam to the drum 20, thereby sterilizing the interior of the drum 20 and the duct assembly 30.

While operating the steam supply 90, the controller 100 can rotate the drum 20 in order to evenly supply steam into the drum 20, and stop the rotation of the circulation fan 43 to sufficiently supply steam to the drum 20.

In some examples, the controller 100 can supply a preset amount of water to the steam supply 90 and operate the steam supply 90 to heat the stored water when power is applied, thereby generating steam for a preset steam spray time ts.

In some examples, the controller 100 can spray steam from the steam supply 90 after the operation of the circulation fan 43 is stopped.

In addition, after stopping the operation of the steam supply 90, the controller 100 can operate the circulation fan 43 again.

In some examples, the controller 100 can drain the condensate by operating the drain pump 62 for a preset drain time after stopping the operation of the steam supply 90.

In some examples, control of the controller 100 over time will be described later with reference to FIGS. 4 and 5.

Figure 4:
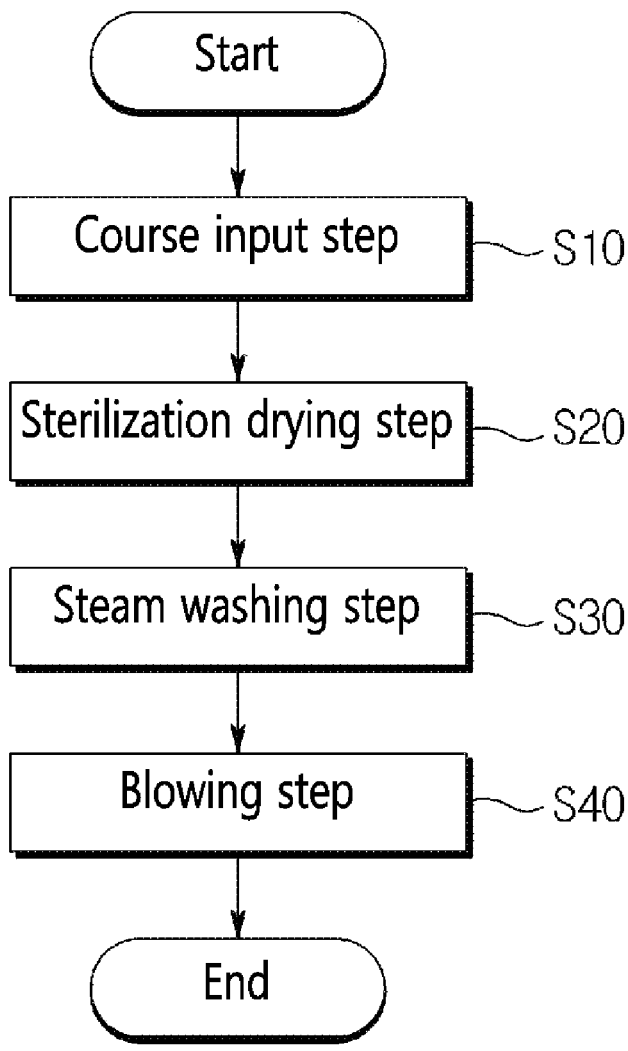
FIG. 4 is a flowchart showing an example of a method for controlling the laundry dryer.
Figure 5B:
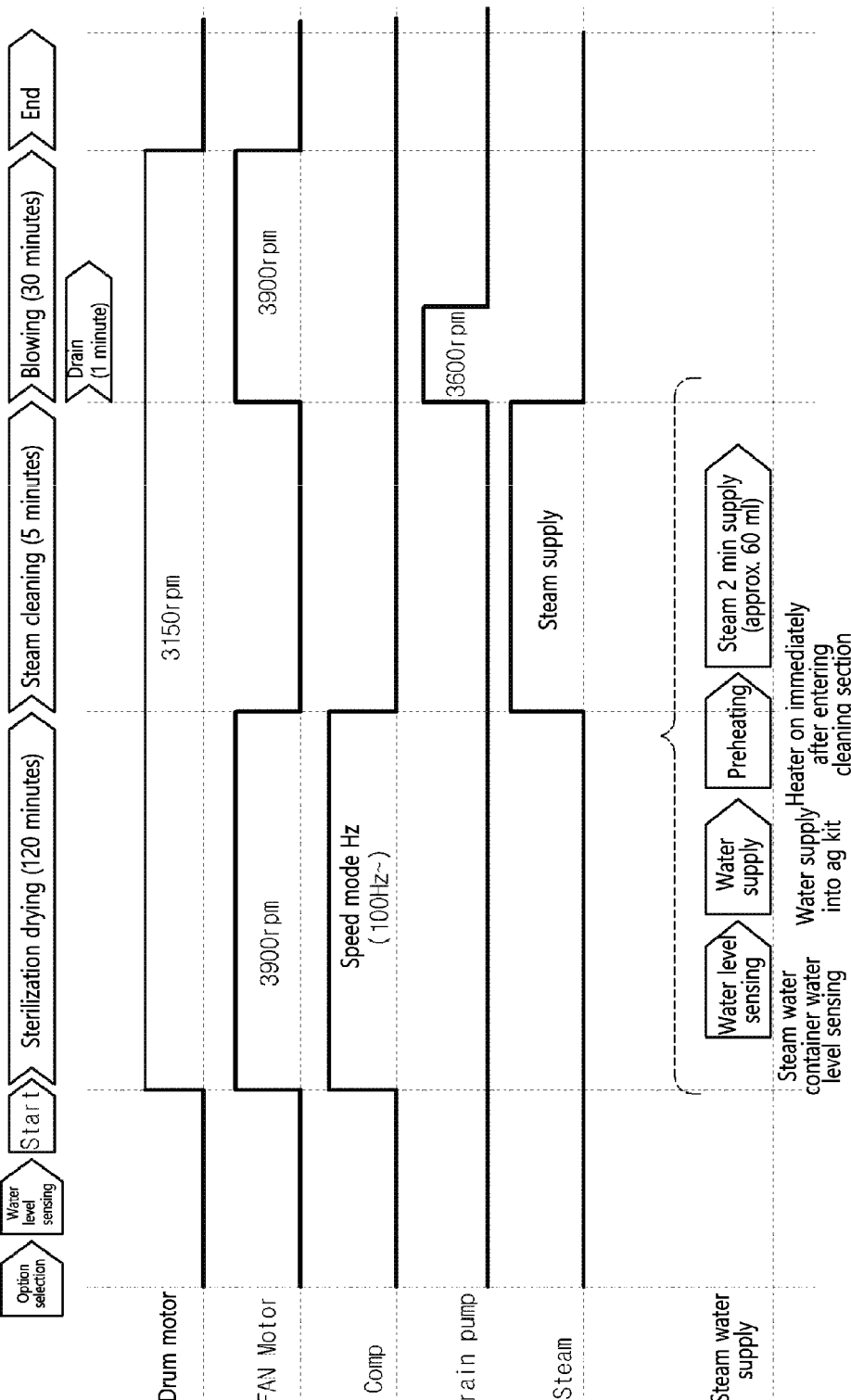

FIG. 4 is a flowchart showing an example of a method for controlling the laundry dryer 1, and FIGS. 5A and 5B respectively examples of a steam drying method.

Referring to FIGS. 1 to 5B, the method for controlling the laundry dryer 1 is as follows.

The method for controlling the laundry dryer 1 can include a course input step (S10), a sterilization drying step (S20), a steam washing step (S30) and a blowing step (S40).

In the course input step (S10), a control input for performing a whole sterilization course for sterilizing the drum 20, a filter F including the first filtration device F1 and the second filtration device F2, and the heat exchange assembly 40 is input.

That is, when the laundry dryer 1 of the present disclosure is turned on, the user can input the control input to the input device 118. In some examples, the user can input the whole sterilization course to remove microorganisms that may exist in the drum 20, the filter F, and the heat exchange assembly 40 by long-term use of the laundry dryer 1.

In some examples, the microorganisms can include *Staphylococcus, Pseudomonas aeruginosa, Escherichia coli*, and house dust mites.

In some examples, in the whole sterilization course, the sterilization operation for the drum 20, the filter F, and the heat exchange assembly 40 can be performed in a state in which a drying target (hereinafter, referred to as the object-to-be-dried) including clothes, towels, and the like is not accommodated in the drum 20.

In some implementations, in the method for controlling the laundry dryer 1, the sterilization operation for the drum 20, the filter F, and the heat exchange assembly 40 can be performed in a no load condition.

The sterilization drying step (S20) can increase the temperature inside the cabinet 10 for the sterilization.

Specifically, the sterilization drying step (S20) can heat the interior of the cabinet 10 for a preset drying time td.

For example, the sterilization drying step (S20) can heat the interior of the cabinet 10 for a duration of 100 minutes or longer and 140 minutes or shorter.

In the sterilization drying step (S20), the controller 100 can rotate the drum motor 51 at a reference speed Wr input in advance (S21). For example, the controller 100 can continuously rotate the drum motor 51 while maintaining the rotation speed of the drum motor 51 at a speed equal to or greater than 3000 rpm and equal to or smaller than 3300 rpm, thereby continuously rotating the drum 20 at a constant speed.

This is to evenly heat the interior of the drum 20 by supplying hot air thereto while rotating the drum 20 at the constant speed.

In the sterilization drying step (S20), the controller 100 can drive (rotate) the compressor 45 in order to raise the internal temperature of the drum 20 (S32).

In some examples, the controller 100 can drive the compressor 45 by adjusting an operating frequency f of the compressor 45 to be within a range of a sterilization frequency fs.

As an example, the controller 100 can drive the compressor 45 at the operating frequency f that is a sterilization frequency fs equal to or higher than 100 Hz.

When activating the sterilization drying step (S20), the controller 100 can drive the compressor 45 at the operating frequency f that is the sterilization frequency fs in order to rapidly increase the internal temperature of the drum 20.

In some examples, the controller 100 can give a control command to increase an output for driving the compressor 45 to the sterilization frequency fs at once. In some implementations, a control command can be given to increase the rotation speed of the compressor motor 45a over several steps in order to prevent malfunction caused by overload of the compressor motor 45a.

As an example, the controller 100 can primarily generate a control command for driving the compressor 45 at a frequency equal to or higher than 55 Hz and equal to or lower than 65 Hz, secondarily generate a control command for driving the compressor 45 at a frequency equal to or higher than 75 Hz and equal to or lower than 85 Hz, and finally generate a control command for driving the compressor 45 at the sterilization frequency fs.

Therefore, the refrigerant of the heat exchange assembly 40 can be compressed at a high temperature and with a high pressure by the driving of the compressor 45, and can exchange the heat with air in the duct assembly 30. As a result, the temperature of air in the duct assembly 30 can be increased.

In some examples, in order to prevent a malfunction or blockage of the power supply caused by an excessive increase in the power consumption of the compressor 45, the controller 100 can measure a refrigerant discharge temperature of the compressor 45 or the temperature of the compressor, and reduce the operating frequency of the compressor 45 when a preset reference temperature is reached.

For example, the controller 100 can measure a top surface temperature of the compressor 45, lower the operating frequency f of the compressor 45 to a frequency equal to or higher than 20 Hz and equal to or lower than 40 Hz when the measured temperature of the compressor 45 reaches 100 degrees Celsius, and drive the compressor 45 at the sterilization frequency fs again when the temperature of the compressor 45 is lowered.

In the sterilization drying step (S20), the controller 100 can operate the circulation fan 43 to circulate air during the heating (S23).

Specifically, in the sterilization drying step (S20), the controller 100 can drive the circulation fan 43 at a preset circulation speed V while the compressor 45 is driven.

For example, in the sterilization drying step (S20), the controller 100 can drive (rotate) the circulation fan 43 at a speed equal to or higher than 3500 rpm and equal to or lower than 4500 rpm while the compressor 45 is driven.

Accordingly, air heated by the driving of the compressor 45 can be circulated while flowing through the drum 20 and the duct assembly 30 by the rotation of the circulation fan 43.

As a result, a temperature T inside the cabinet 10 can increase to a temperature equal to or higher than a sterilization temperature Ts for sterilizing the microorganisms or the like present in the drum 20 and the duct assembly 30 by the driving of the compressor 45 and the circulation fan 43 (T≥Ts). The sterilization can refer to getting rid of or reducing living microorganisms.

For example, in the sterilization drying step (S20), the internal temperature of the cabinet 10 can be increased until a temperature of a heat exchanger (which can refer to an evaporator 41) in a direction in which air is introduced from the drum 20 becomes a temperature equal to or higher than 60 degrees Celsius.

In the sterilization drying step (S20), the controller 100 can supply water from the water supply 80 to the steam supply 90 (S24).

In some implementations, controller 100 can determine whether to supply water by measuring a water level inside the steam generator 91.

That is, the controller 100 can be configured not to supply water to the steam generator 91 when the amount of water stored in the steam generator 91 is equal to or greater than an amount to be sprayed in the steam washing step (S30) to be described later, but supplies water from the water supply 80 to the steam generator 91 when the amount of water stored in the steam generator 91 is smaller than the amount of water to be sprayed in the steam washing step (S30) to be described later.

In some examples, the controller 100 can operate a water supply pump disposed in the internal water supply 81 to thereby supply water into the steam generator 91, and can open the direct water valve 82a disposed in the external water supply 82 so as to supply water into the steam generator 91.

For example, the controller 100 can supply water of an amount equal to or greater than 50 cc from the water supply 80 to the steam generator 91, and a time for supplying water of the water supply 80 to the steam generator 91 can be 20 seconds or longer and 40 seconds or shorter.

As another example for supplying sufficient water, the controller 100 can supply water of an amount equal to or greater than 150 cc and equal to or smaller than 250 cc from the water supply 80 to the steam generator 91, and a time for supplying water of the water supply 80 to the steam generator 91 can be 40 seconds or longer and 1 minute 20 seconds or shorter.

Therefore, in the sterilization drying step (S20), the controller 100 can operate the drum 20, the compressor 45, and the circulation fan 43 to increase the temperature inside the cabinet 10 including the drum 20 and the duct assembly 30 and increase the temperatures of the drum 20, the filter F, and the heat exchange assembly 40 to a temperature equal to or higher than the sterilization temperature Ts.

The steam washing step (S30) can supply steam into the drum 20 for the sterilization inside the drum 20 and the duct assembly 30 after the sterilization drying step (S20).

In the steam washing step (S30), the controller 100 can continuously rotate the drum motor 51 at the reference speed Wr input in advance (S31). For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at a constant speed.

Therefore, when steam is sprayed while the drum 20 continues to rotate, steam can be evenly supplied into the drum 20 and the interior of the drum 20 can be sterilized evenly.

In the steam washing step (S30), the controller 100 can be configured not to drive the compressor 45 in order to prevent the instantaneous increase in the power consumption of the laundry dryer 1 (S32).

In the steam washing step, the controller 100 can stop the operation of the circulation fan 43 that was operating in the sterilization drying step (S20) (S33).

Accordingly, the circulation of air circulating inside the drum 20 and the duct assembly 30 can be stopped, and steam sprayed from the steam supply 90 can be sufficiently supplied to the drum 20.

In the steam washing step (S30), the controller 100 can operate the steam supply 90 to supply steam into the drum 20 (S34).

The steam washing step (S30) includes a steam preheating step (S34a) and a steam spraying step (S34b).

In the steam preheating step (S34a), the controller 100 can apply power to the steam supply 90 to heat water supplied for the steam generation for a preset preheating time th.

In detail, in the steam preheating step (S34a), the controller 100 can heat water supplied to the steam generator 91 by applying power to a heater disposed in the steam generator 91. In some implementations, the controller 100 can apply power to the heater during the preheating time th, and the preheating time th can be set to be equal to or longer than a time for water to reach a boiling point.

For example, in the steam preheating step (S34a), the controller 100 can generate a control command to apply power to the steam supply 90 for 2 minutes and 30 seconds or longer and 3 minutes and 30 seconds or shorter.

In the steam spraying step (S34b), the controller 100 can spray steam generated from the steam supply 90 into the drum 20 as much as a preset spraying amount after the steam preheating step (S34a).

Specifically, in the steam spraying step (S34b), the controller 100 can generate a control command to the steam generator 91 such that water heated in the steam generator 91 and started to boil flows through the steam pipe 92 and is sprayed into the drum body 21 via the steam nozzle 93.

For example, in the steam spraying step (S34b), the controller 100 can spray water of an amount equal to greater than 50 cc and equal to or smaller than 70 cc from the steam generator 91 into the drum 20. In some implementations, a time for spraying steam can be 1 minute 30 seconds or longer and 2 minutes 30 seconds or shorter.

Therefore, in the steam washing step (S30), the controller 100 can operate the drum 20 and the steam supply 90 to evenly supply high-temperature steam into the drum 20 to remove bacteria and the like.

The blowing step (S40) can sterilize the entire filter F and the entire heat exchange assembly 40 arranged in the duct assembly 30 at a high temperature by circulating air inside the drum 20 after the steam washing step (S30).

For example, the blowing step (S40) can circulate air inside the drum 20 and the duct assembly 30 for 20 minutes or longer and 40 minutes or shorter so as to supply heat and enthalpy to the filter F and the heat exchange assembly 40.

In the blowing step (S40), the controller 100 can continuously rotate the drum motor 51 at the reference speed Wr input in advance (S41). For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at the constant speed.

Therefore, air circulating in the drum 20 and the duct assembly 30 can sterilize the interior of the drum 20 evenly.

In the blowing step (S40), the controller 100 can be configured not to drive the compressor 45 in order to improve a power efficiency (S42).

In the blowing step (S40), the controller 100 can rotate the circulation fan 43 to circulate air that has obtained high heat or high enthalpy in the sterilization drying step (S20) and the steam washing step (S30) (S43).

Specifically, in the blowing step (S40), the controller 100 can drive the circulation fan 43 at the preset circulation speed V.

For example, in the blowing step (S40), the controller 100 can drive (rotate) the circulation fan 43 at a speed equal to or higher than 3500 revolutions per minute (rpm) and equal to or lower than 4500 rpm while the compressor 45 is driven.

In the blowing step (S40), because sufficient moisture has been supplied to the object-to-be-dried, the controller 100 can be configured not to operate (stop the operation of) the steam supply 90 (S44).

Therefore, air that has obtained the high heat or the high enthalpy in the sterilization drying step (S20) and the steam washing step (S30) can be circulated while flowing through the drum 20 and the duct assembly 30 by the rotation of the circulation fan 43.

As a result, according to the blowing step (S40) of the present disclosure, surface temperatures of the drum 20, the filter F, and the heat exchange assembly 40 can be increased to a temperature equal to or higher than the sterilization temperature Ts for removing the microorganisms or the like, and can be maintained for the reference time ts for the sterilization or longer.

For example, the blowing step (S40) can maintain the surface temperatures of the drum 20, the filter F, and the heat exchange assembly 40 for 10 minutes or longer at a temperature equal to or higher than 60 degrees Celsius.

In some examples, in the blowing step (S40), the controller 100 can operate the drain pump 62 to discharge the condensate collected in the cabinet 10 (S45).

In the blowing step (S40), the controller 100 can drain the condensate for a preset drainage time td when activating the blowing step (S40).

That is, the controller 100 can operate the drain pump 62 to move the condensate collected in the water collecting portion 60 to the water storage tank 72.

In some examples, the drainage time td can be 50 seconds or longer and 70 seconds or shorter.

Figure 6:
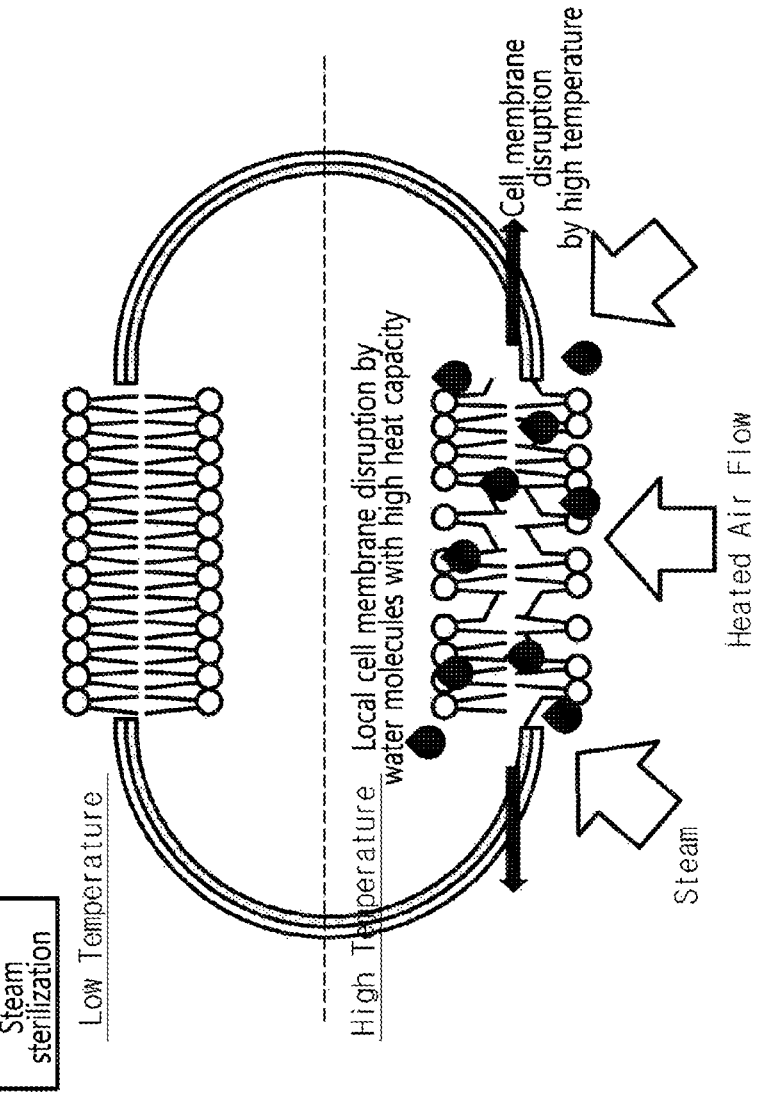
FIG. 6 is a view for illustrating a sterilization principle based on the method for controlling the laundry dryer.
Figure 7:
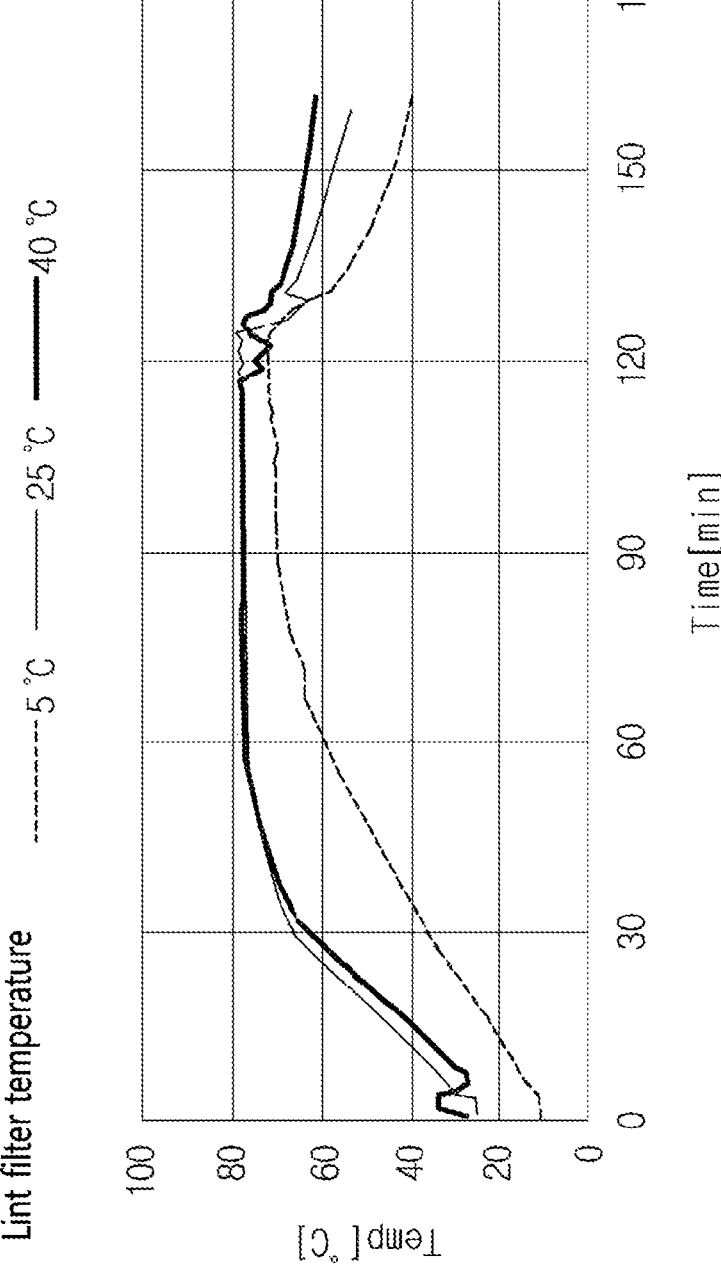
FIG. 7 is a graph showing an example of a temperature of a filter based on the method for controlling the laundry dryer.
Figure 8:
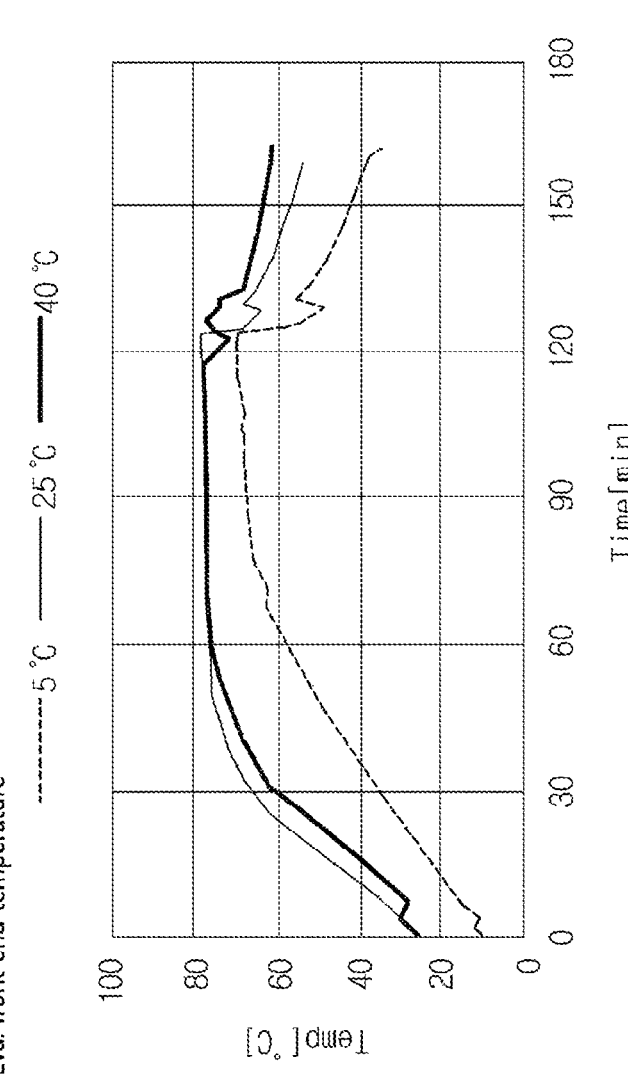
FIG. 8 is a graph showing an example of a temperature of a front end of an evaporator based on the method for controlling the laundry dryer.

FIG. 6 is a view for illustrating a sterilization principle based on a method for controlling a laundry dryer, FIG. 7 is a graph about a temperature of a filter based on a method for controlling a laundry dryer, and FIG. 8 is a graph about a temperature of a front end of an evaporator based on a method for controlling a laundry dryer.

Sterilization effects will be described with reference to FIGS. 1 to 8 as follows.

First, an effect on each component of the present disclosure is as follows.

According to the method for controlling the laundry dryer 1, the drum 20 of the present disclosure is controlled to rotate while maintaining the constant speed in the sterilization drying step (S20), the steam washing step (S30), and the blowing step (S40) (S21, S31, S41).

In some implementations, the drum 20 continues to rotate after the sterilization drying step (S20). Therefore, hot air and steam for the sterilization can be evenly supplied to an inner surface of the drum 20, and the drum 20 can be evenly sterilized.

In some examples, the compressor 45 of the present disclosure is driven in the sterilization drying step (S20) (S22) so as to heat air inside the drum 20 and the duct assembly 30 and then the driving of the compressor 45 is terminated to reduce the power consumption (S32, S42).

The compressor 45 heats air flowing inside the drum 20 and the duct assembly 30 to provide hot air (heat) supplied into the drum 20 and the duct assembly 30. Therefore, surfaces of the drum 20, the filter F, and the heat exchange assembly 40 are heated via the driving of the compressor 45, and the surfaces of the drum 20, the filter F, and the heat exchange assembly 40 are sterilized by the supply of the high-temperature heat.

In some examples, the circulation fan 43 of the present disclosure starts to rotate in the sterilization drying step (S20) (S23), stops rotating in the steam washing step (S30) (S33), and rotates again in the blowing step (S40) (S43).

The circulation fan 43 can be controlled independently of the rotation of the drum 20. For example, the circulation fan 43 can rotate when the air heated by the driving of the compressor 45 is circulated, and stop rotating during the steam spray when the flow of air is unnecessary.

Therefore, the circulation fan 43 can improve a supply efficiency of steam so that a sterilization efficiency of the drum 20 is improved.

The steam supply 90 of the present disclosure is operated for the preheating and the steam spraying for the steam generation in the steam washing step (S30) (S34).

In the present disclosure, the sterilization effect of the steam spray is as follows.

When hot air is supplied to the drum 20 and the duct assembly 30 in the sterilization drying step (S20), the temperature inside the drum 20 reaches the sterilization temperature (which can be equal to or higher than 60 degrees Celsius) for the sterilization. In some examples, when the steam supply 90 sprays high-temperature steam to the drum 20 in the steam washing step (S30) of the present disclosure, the enthalpy of the air inside the drum 20 is increased, and the microorganisms including the bacteria are sterilized by being exposed to the high heat.

That is, according to the steam washing step (S30), as steam with high heat capacity is supplied into the drum 20 heated to have the temperature equal to or higher than the sterilization temperature Ts, the microorganisms such as the bacteria are exposed to high enthalpy, and as a result, the microorganisms such as the bacteria die as cell membranes thereof are destroyed (see FIG. 6).

Thereafter, by circulating air of the drum 20 and the duct assembly 30 via the blowing step (S40), the surface temperatures of the drum 20, the filter F, and the heat exchange assembly 40 can be maintained at the temperature equal to or higher than the sterilization temperature (60 degrees Celsius) for the reference time (ts: 10 minutes) for the sterilization or longer (see FIGS. 7 and 8). Therefore, the microorganisms present on the surfaces of the drum 20, the filter F, and the heat exchange assembly 40 can be exposed to energy of high heat, so that cells thereof can be destroyed and the microorganisms and the like will die. Hereinabove, the present disclosure has been described in detail through a specific implementation, but this is for specifically illustrating the present disclosure, and the present disclosure is not limited thereto. It is clear that the present disclosure can be modified or improved by a person having ordinary knowledge in the field within the technical spirit of the present disclosure.

All simple modifications or changes of the present disclosure fall within the scope of the present disclosure, and the specific protection scope of the present disclosure will be clarified by the appended claims.

The invention claimed is:

1. A method for controlling a laundry dryer, the laundry dryer including a cabinet that defines an outer appearance of the laundry dryer, a drum disposed inside the cabinet and configured to accommodate an object to be dried therein, a duct assembly configured to circulate air discharged from the drum to the drum, a circulation fan configured to provide a flow force to the air moving along the duct assembly, a heat exchange assembly disposed in the duct assembly and configured to exchange heat with the air circulated along the duct assembly, and a compressor configured to compress a refrigerant to exchange heat with the air circulated along the duct assembly, and a steam device configured to supply steam into the drum, the method comprising:

increasing a temperature inside the cabinet for sterilization of the drum;

supplying steam into the drum for sterilization of the drum after increasing the temperature inside the cabinet; and circulating air inside the drum after supplying the steam into the drum, wherein increasing the temperature inside the cabinet, supplying the steam into the drum, and circulating the air inside the drum are performed while rotating the drum based on no laundry load being applied to the drum, wherein increasing the temperature inside the cabinet and circulating the air inside the drum are performed while operating the circulation fan, wherein supplying the steam into the drum is performed while the circulation fan is stopped, and wherein circulating the air inside the drum comprises operating a drain pump to thereby drain condensate water collected in the cabinet.

2. The method of claim 1, wherein increasing the temperature inside the cabinet comprises driving the compressor to thereby increase the temperature inside the cabinet.

3. The method of claim 1, wherein supplying the steam into the drum comprises operating a steam supply to supply the steam into the drum.

4. The method of claim 3, wherein supplying the steam into the drum comprises:

preheating the steam supply; and spraying the steam into the drum.

5. The method of claim 1, wherein supplying the steam into the drum comprises rotating the drum to thereby sterilize an inside of the drum.

6. The method of claim 1, wherein increasing the temperature inside the cabinet comprises:

increasing the temperature of the cabinet until a temperature of the heat exchange assembly becomes greater than or equal to 60 degrees Celsius, the heat exchange assembly being disposed at a position receiving air discharged from the drum.

7. The method of claim 1, wherein rotating the drum comprises maintaining a constant speed of the drum while increasing the temperature inside the cabinet, supplying the steam into the drum, and circulating the air inside the drum.

* * * * *